United States Patent [19]

Nazimok et al.

[11] Patent Number: 5,359,133
[45] Date of Patent: Oct. 25, 1994

[54] PROCESS FOR PRODUCING HIGHLY PURIFIED BENZENEDICARBOXYLIC ACID ISOMERS

[75] Inventors: Vladimir F. Nazimok; Nadezhda N. Goncharova; Valerij P. Yurjev; Vladimir D. Manzurov, all of Tula, Russian Federation

[73] Assignees: Joint-Stock Company of Research and Design Institute of Monomers (AO NIPIM), U.S.S.R.; Samsung General Chemical Co., Ltd. Rep. of Korea

[21] Appl. No.: 141,738

[22] Filed: Oct. 27, 1993

[30] Foreign Application Priority Data

Sep. 28, 1993 [RU] Russian Federation ........... 93046191
Sep. 28, 1993 [RU] Russian Federation ........... 93046190

[51] Int. Cl.$^5$ .............................................. C07C 51/16
[52] U.S. Cl. ..................................... 562/413; 562/487
[58] Field of Search ................. 562/413, 487, 486, 416

[56] References Cited

U.S. PATENT DOCUMENTS

| | | | |
|---|---|---|---|
| 3,595,908 | 7/1971 | Lumbroso | 562/413 |
| 3,845,117 | 10/1974 | Kollar | 562/413 |
| 3,859,344 | 1/1975 | Shigeyasu | 562/413 |
| 4,201,871 | 5/1980 | Tanouchi | 562/413 |
| 4,286,101 | 8/1981 | Hashizume | 562/413 |
| 4,314,073 | 2/1982 | Crooks | 562/413 |
| 4,334,086 | 6/1982 | Hanotier | 562/413 |
| 4,594,449 | 6/1986 | Takuma | 562/413 |
| 4,772,748 | 9/1988 | Hashizume et al. | |
| 4,877,900 | 10/1989 | Tamaru | 562/413 |
| 4,892,970 | 1/1990 | Nowicki | 562/413 |
| 5,132,450 | 7/1992 | Tanaka | 562/413 |

FOREIGN PATENT DOCUMENTS

| | | |
|---|---|---|
| 1270030 | 6/1968 | Fed. Rep. of Germany . |
| 63-23982B | 1/1982 | Japan . |
| 60-233032A | 11/1985 | Japan . |
| 62-270548A | 11/1987 | Japan . |

*Primary Examiner*—Michael L. Shippen
*Attorney, Agent, or Firm*—Nixon & Vanderhye

[57] ABSTRACT

Disclosed herein is a process for producing highly purified benzenedicarboxylic acid isomers without an additional catalytic reductive purification step, which comprises (a) an oxidation step wherein xylene isomer is oxidized with molecular oxygen or molecular oxygen containing gas in the presence of a catalyst system composed of cobalt, manganese, bromine and at least one selected from nickel, chromium, zirconium and cerium in lower aliphatic carboxylic acid; and (b) an extraction/post-oxidation step wherein the oxidation product is crystallized to give cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°–80° C. lower than that of said heating, each of said oxidation and extraction/post-oxidation being carried out once or twice, provided that any one or both of said steps should be carried out twice. According to the invention, the solvent employed to extract impurities is recycled from the subsequent oxidation steps.

19 Claims, 3 Drawing Sheets

PROCESS FOR PRODUCING HIGHLY PURIFIED BENZENEDICARBOXYLIC ACID ISOMERS

BACKGROUND OF THE INVENTION

1. Field of the Invention

The present invention relates to an organic synthesis, more particularly it relates to an improved process for producing highly purified benzenedicarboxylic acids isomers including terephthalic acid(TA), isophthalic acid(IA) and phthalic acid(PA), which are the most important monomers and semiproducts in a polymer chemistry for plastic, chemical fiber, film, varnishes and dyes.

2. Description of the Prior Art

Terephthalic acid is useful as a starting material for producing polyester films and fibers and is commonly produced by the so-called SD process wherein paraxylene is oxidized with molecular oxygen in the presence of catalysts containing heavy metals in acetic acid solvent. However, since the terephthalic acid produced from the SD process contains high content (1000-3000 ppm) of 4-carboxybenzaldehyde(hereinafter referred to as "4-CBA"), it is not a suitable starting material for producing polyester films and fibers.

Therefore, a method has been adopted in which terephthalic acid is reacted with methanol to form dimethyl terephthalate which is easily purified, and after purifying thereof, the dimethyl terephthalate is reacted with glycol to produce polyester. An alternative method which is more widely used for purifying terephthalic acid comprises the steps of dissolving the terephthalic acid in water at high temperature and pressure, treating the resulting solution with hydrogen over noble metal catalysts such as palladium in order to obtain highly purified terephthalic acid which contains less than 25 ppm of 4-CBA. However, the known processes have drawbacks; the former method produces methanol during the preparation process of polyester and the latter method requires two separate plants, each for oxidizing and for purifying, since the conditions of oxidation and purification, for example solvent, catalysts and operation conditions are different from each other.

Up to now, several methods have been proposed to avoid difficulties involved in these conventional processes.

Methods for producing terephthalic acid without reductive purification step wherein paraxylene is oxidized with molecular oxygen via consecutive 4 steps in the presence of cobalt-manganese-bromine catalyst in acetic acid had been proposed. [U.S. Pat. No.4772748, JP 62-270548A and JP 63-23982B] According to these methods, the paraxylene, in the first oxidation step, is oxidized at 180°-230° C. for 40-150 minutes with the conversion of more than 95%; in the second oxidation step, is oxidized at a temperature of lower than that in the first reaction vessel by 2°-30° C. for 20-90 minutes; in the third oxidation step, is oxidized at 235°-290° C. for 10-60 minutes; and the final fourth oxidation step, is oxidized at 260° C. Since the TA produced by this method contains 0.027% of 4-CBA, it cannot be directly used for producing polyester fibers and films. Moreover, the above method has several disadvantages: a) since the high temperature (ca. 260° C.) employed for oxidizing impurities in the third and fourth oxidation steps also causes oxidation of acetic acid solvent, the method is unfavorable in view of technology and economics; b) rather long reaction time in the first oxidation step decreases the efficiency of the process; and c) the content of 4-CBA contained in the TA as an impurity is still high (0.027%).

Accordingly, the above method is disadvantageous in that the efficiency of the process is relatively low and less purified TA is produced compared with the conventional method employing the reductive purification step.

Another method is proposed wherein paraxylene is oxidized with molecular oxygen in the presence of heavy metal compounds and a bromine compound in acetic acid medium with a conversion of higher than 90%, then the resulting mixture is crushed at 140°-230° C. in the molecular oxygen atmosphere to reduce the average diameter of terephthalic acid particles by more than 20% (the first purification step) followed by the second step wherein the slurry obtained in the first purification step is oxidized with molecular oxygen at a temperature of at least 10° C. higher than that of the previous step and between 180 and 300° C. [JP 60-233032A] The method gives pure TA which can be directly employed for the polymerization.

However, the method requires a separate equipment for crashing the terephthalic acid, for example an agitator of high speed rotation. Moreover, it is difficult to produce highly pure terephthalic acid containing 4-CBA of less than 0.0025%.

Further, another method has been proposed wherein the crude product slurry produced by liquid phase catalytic oxidation of paraxylene is treated with molecular oxygen in acetic acid medium in the presence of catalyst composed of compounds of cobalt, manganese, chromium, cerium, lead or their mixtures, the mount of said catalyst being 0.01-5.0% by weight of TA to be purified. [Germany Pat. No. 1270030] The method is disadvantageous in that since the treatment is effected at a temperature as high as 250° C. for 1 hour, the acetic acid as well as impurities are oxidized.

Accordingly, there has been a need to provide an improved method for producing highly purified benzenedicarboxylic acid isomers without additional catalytic purification step.

SUMMARY OF THE INVENTION

Thus, an object of the invention is to provide a process for producing highly purified benzenedicarboxylic acid isomers without an additional catalytic reductive purification step, which comprises (a) an oxidation step wherein xylene isomer is oxidized with molecular oxygen or molecular oxygen containing gas in the presence of a catalyst system composed of cobalt, manganese, bromine and at least one selected from nickel, chromium, zirconium and cerium in a lower aliphatic carboxylic acid; and (b) an extraction/post-oxidation step wherein the oxidation product is crystallized to separate a cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system, at a temperature of 2°-80° C. lower than that of said heating, each of said oxidation and extraction/post-oxidation steps being carded out once or twice, provided that any one or both of said steps should be carded out twice.

Another object of the invention is to provide a process for producing highly purified benzenedicarboxylic acid isomers without an additional catalytic reductive purification step, which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in a lower aliphatic carboxylic acid; (b) the second oxidation step wherein the product obtained from the first oxidation step is reoxidized with said catalyst system; and (c) the first extraction/post-oxidation step wherein the product obtained from the second oxidation step is crystallized to separate a cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system at a temperature of 2°–80° C. lower than that of said heating.

Another object of the invention is to provide a process for producing highly purified benzenedicarboxylic acid isomers without an additional catalytic reductive purification step, which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in a lower aliphatic carboxylic acid; (b) the second oxidation step wherein the product obtained from the first oxidation step is reoxidized with said catalyst system; (c) the first extraction/post-oxidation step wherein the product obtained from the second oxidation step is crystallized to separate cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system at a temperature of 2°–80° C. lower than that of said heating; and (d) the second extraction/post-oxidation step wherein the product obtained from the first extraction/post-oxidation step is crystallized to separate a cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system at a temperature of 2°–80° C. lower than that of said heating.

Another object of the invention is to provide a process for producing highly purified benzenedicarboxylic acid isomers without an additional catalytic reductive purification step, which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in a lower aliphatic carboxylic acid; (b) the first extraction/post-oxidation step wherein the product obtained from the first oxidation step is crystallized to separate a cake of benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system at a temperature of 2°–80° C. lower than that of said heating; and (c) the second extraction/post-oxidation step wherein the product obtained from the first extraction/post-oxidation step is crystallized to separate a cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system at a temperature of 2°–80° C. lower than that of said heating.

DETAILED DESCRIPTION OF THE PREFERRED EMBODIMENTS

Figure 1:
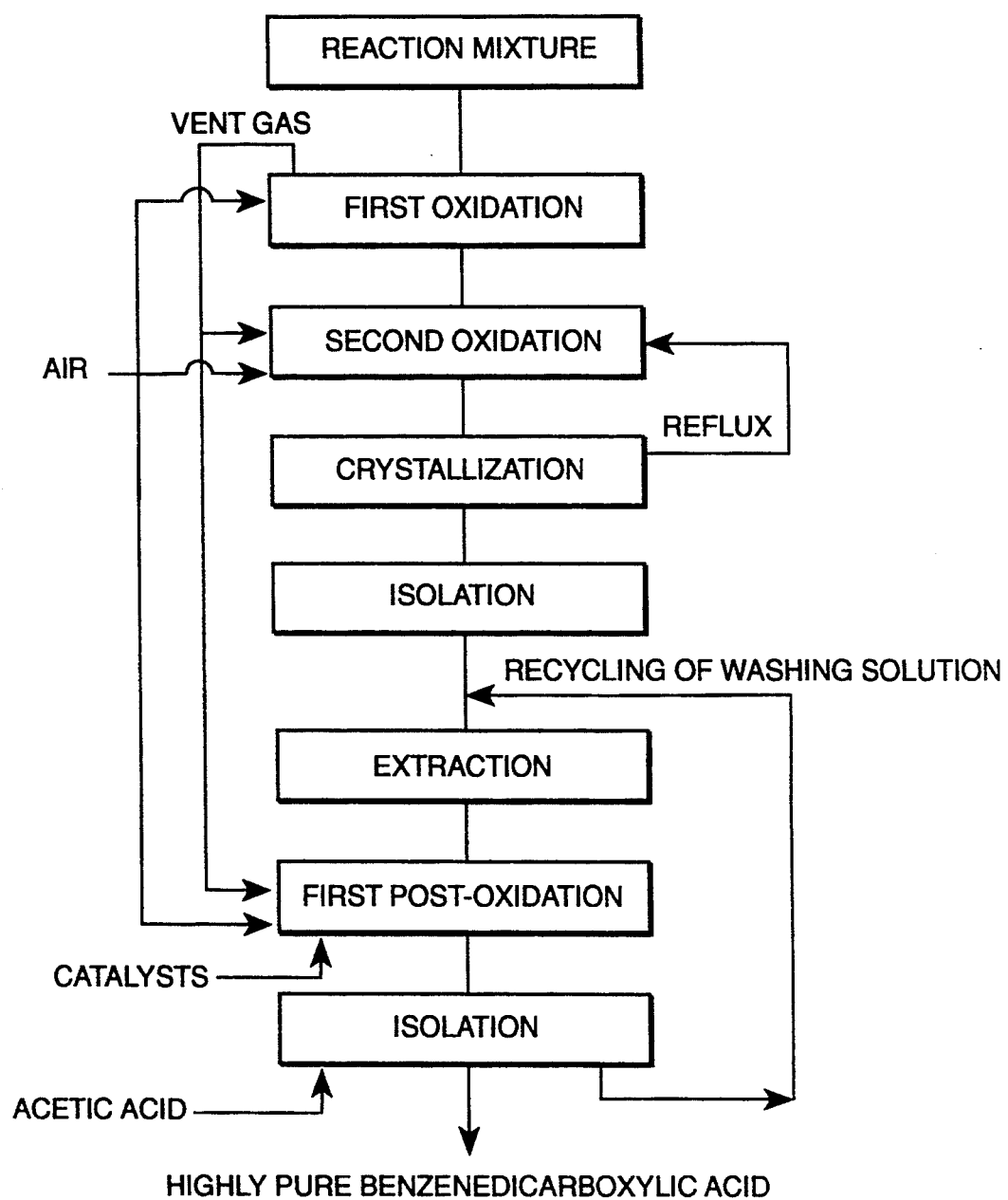
FIG. 1 shows a flow chart of the process according to the invention wherein the oxidation step is carded out twice and then the extraction/post-oxidation step is carried out once.(Method 1)
Figure 2:
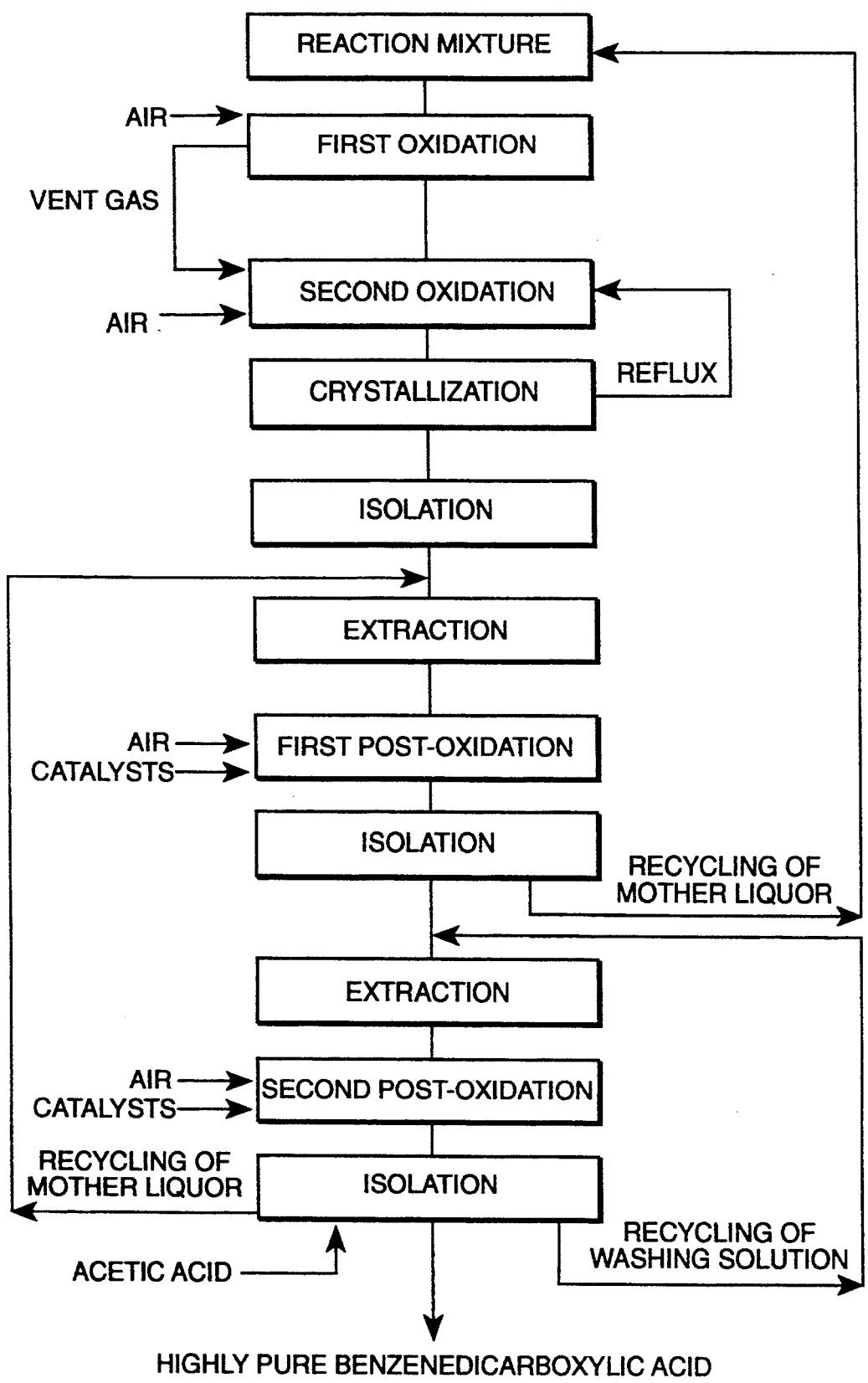
FIG. 2 shows a flow chart of the process according to the invention wherein the oxidation step is carried out twice and then the extraction/post-oxidation step is carried out twice.(Method 2)
Figure 3:
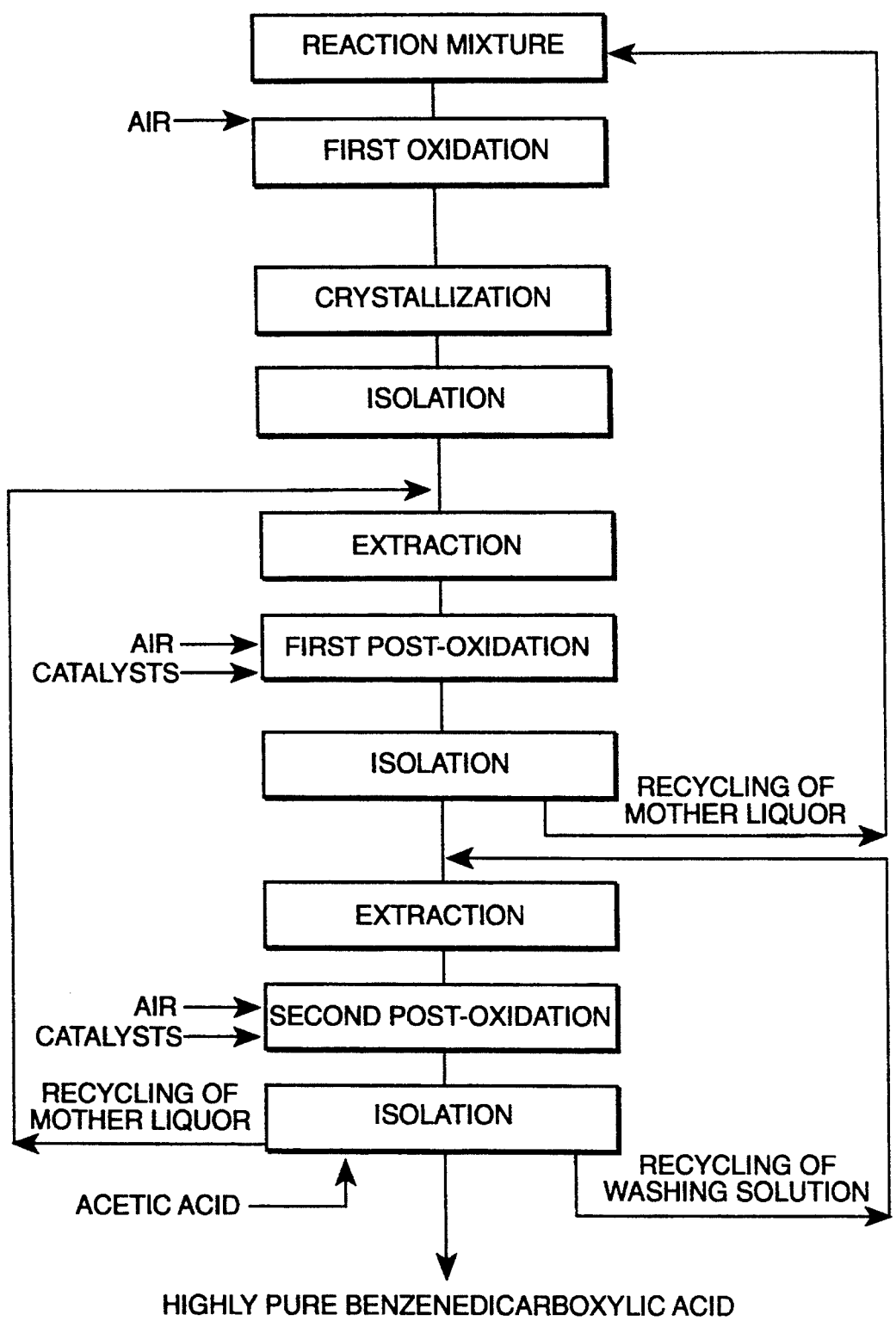
FIG. 3 shows a flow chart of the process according to the invention wherein the oxidation step is carded out once and the extraction/post-oxidation step is carried out twice. (Method 3)

According to the process of the invention, an oxidation step wherein xylene isomer is oxidized with molecular oxygen or molecular oxygen containing gas in the presence of a catalyst system composed of cobalt, manganese, bromine and at least one selected from nickel, chromium, zirconium and cerium in a lower aliphatic carboxylic acid is carried out once or twice and an extraction/post-oxidation step wherein the oxidation product is crystallized to separate a cake of crude benzenedicarboxylic acid isomer, the cake is reslurried by adding a lower aliphatic carboxylic acid solvent thereto followed by heating in order to extract impurities contained therein into the solvent, and the resulting slurry is oxidized with said catalyst system is carded out once or twice, provided that any one or both of said steps should be carded out twice.

The process according to the invention my be summarized as Method 1 wherein the oxidation step is carried out twice and the extraction/post-oxidation step is carded out once, Method 2 wherein the oxidation step is carded out twice and the extraction/post-oxidation step is carded out twice and Method 3 wherein the oxidation step is carded out once and the extraction/post-oxidation step is carded out twice.

The term "extraction/post-oxidation step" employed herein means that a process which consists of an extraction step wherein the product from the first or second oxidation step is crystallized to separate a cake of crude benzenedicarboxylic acid isomer, the cake is reslurried by adding a lower aliphatic carboxylic acid solvent thereto followed by heating in order to extract impurities contained therein into the solvent and an oxidation step wherein the slurry resulted from the extraction step is oxidized with a catalyst system. According to the invention, the catalyst system used in this oxidation step(post-oxidation step) is the same as that of used in the first or second oxidation step.

Hereinafter, the methods according to the invention shall be described in detail.

The xylene isomers used as a starting material in the methods of the present invention may include ortho-, metha- and para-isomers and these isomers give corresponding carboxybenzaldehydes(hereinafter referred to as "CBA") as impurities in the oxidation step. Thus, if para-, metha- or ortho-xylene is employed as a starting material, 4-CBA, 3-CBA or 2-CBA is respectively produced.

In accordance with the process of the invention, a reaction mixture composed of xylene isomer, lower aliphatic carboxylic acid and catalysts is preheated to a temperature of higher than 150° C. and lower than the temperature of the first oxidation reaction and then is introduced into the first oxidation reaction vessel at a linear velocity of 6-30 m/s in a counter direction to the direction of revolution of the fluid in the reaction vessel.

The oxidation reaction is carded out in a lower aliphatic carboxylic acid by using molecular oxygen or a molecular oxygen containing gas at 150°-230° C. for about 20-60 minutes in the presence of a catalysts system composed of cobalt-manganese-bromine and one or more selected from nickel, chromium, zirconium and cerium.

As molecular oxygen or molecular oxygen containing gas employed in the present invention, oxygen or air is employed, and a mixture of air and the vent gas resulted from the first oxidation is employed in the second oxidation or in the first or second extraction/post-oxidation.

As a lower aliphatic carboxylic acid employed as a medium as well as an extracton solvent in the process of the present invention, there may be included an aliphatic acid containing 1 to 6 carbon atoms, for example acetic acid, butanoic acid, pentanoic acid or hexanoic acid, and acetic acid is preferred.

The catalyst system employed according to the invention essentially consists of cobalt, manganese and bromine, and further comprises one or more heavy metals selected from nickel, chromium, zirconium or cerium. The example of cobalt compounds may include, not intended to be limited thereto, cobalt acetate or cobalt naphthenate. The example of manganese compounds may include, not intended to be limited thereto, manganese acetate or manganese naphthenate. The example of bromine compounds may include, not intended to be limited thereto, sodium bromide or tetrabromoethane, or a mixture of bromine compounds and chlorine compounds in a ratio of 1:0.001-0.5 in terms of bromine and chlorine. The chlorine compounds my include, not intended to be limited thereto, $ZrOCl_2$, $NiCl_26H_2O$ or hydrochloric acid, and may be added per se or in a salt form with zirconium or nickel which is employed as a component of catalyst system.

The heavy metal employed as a component of the catalyst system according to the invention may be in the form of any salt which can be dissolved in a lower aliphatic carboxylic acid, particularly acetic acid, and preferably is in the form of acetate. The ratio of each components of the catalyst varies according to the each oxidation steps as illustrated hereinafter.

In the case where the oxidation step is carded out twice, the slurry obtained from the first oxidation step is oxidized for 10-30 minutes by using the catalyst system same as that used in the first oxidation, a vent-gas from the first oxidation reactor, air and a reflux resulted from the crystallization step alter the second oxidation.

In the extraction/post-oxidation step, the solvent contained in the slurry is replaced with new solvent followed by heating (Extraction step). The heating is carded out in order to extract impurities contained in the slurry. After heating, the slurry containing the extracted impurities is cooled and oxidized with the same catalyst system as that used in the oxidation step. (Post-oxidation step) The extraction/post-oxidation may be carded out once or twice.

The extraction/post-oxidation step according to the invention will be described in more detail as follows.

In the extraction/post-oxidation process, the slurry of crude benzenedicarboxylic acid isomers obtained from the first or second oxidation step is isolated to give a cake and the cake is reslurried with the lower aliphatic carboxylic acid which is obtained in isolating or washing the cake from the slurry resulted from the extraction/post-oxidation step. After reslurrying, the resulting slurry is treated under heating to a temperature of 200°-280° C. for 5-60 minutes to extract the Wittic acid and CBA contained in the benzenedicarboxylic acid isomer crystals as impurities. In this case, the aliphatic carboxylic acid recycled from the isolating or washing step to reslurry the cake should be used in such an mount that more than 60% of the lower aliphatic carboxylic acid contained in the slurry from the previous oxidation step can be replaced with.

Thus obtained impurities-containing slurry from the extraction by heating is subjected to oxidation by using the catalyst system and molecular oxygen containing gas at a temperature which is lower 2°-80° C. than that of the extraction for 10-30 minutes and the resulting slurry is isolated and washed.

The above extraction/post-oxidation step can be effected once or twice and consequently the composition and concentration of the catalyst system, the source from which the lower aliphatic carboxylic acid which is used for reslurrying and the concentration of the impurity contained in the crude benzenedicarboxylic acid obtained from each oxidation step vary. However, in any cases, highly purified benzenedicarboxylic acid which contains less than 0.0025% of carboxybenzaldehyde is finally produced and for this purpose at least one or both of the oxidation and extraction/post-oxidation steps should be effected twice.

The reaction conditions of the above-mentioned Methods 1, 2, and 3 will be explained in more detail as follows.

In Method 1, the catalyst system employed in the post-oxidation step has a ratio of [Mt], a concentration of heavy metal added to cobalt-manganese-bromine component to [Co+Mn], a concentration of cobalt plus manganese of 1:0.01-0.2 and the total concentraion of heavy metal(s) added is 50-300 ppm. The concentration of heavy metals employed in the first oxidation:second oxidation:first extraction/post-oxidation is 1:0.5-0.9:0.- 05-0.20. The solvent for reslurrying the cake from the second oxidation step is recycled from the washing step for washing the cake resulted from the first extraction/post-oxidation step. The recycled solvent should be used in such an mount that at least 60% of the lower carboxylic acid contained in the slurry from the second oxidation step can be replaced with.

Where Method 1 is employed for producing highly pure benzenedicarboxylic acid, the concentration of CBA as an impurity contained in the crude benzenedicarboxylic acids produced from the first oxidation, second oxidation and first extraction/post-oxidation is 0.06-0.16%, 0.03-0.08% and less than 0.0025%, respectively.

In Method 2, the ratio of [Co+Mn] to [Mt] is 1:0.01–0.2 and the total concentraion of heavy metal(s) added is 30–200 ppm. The concentration of heavy metal(s) employed in the first oxidation: second oxidation: first extraction/post-oxidation:second extraction/post-oxidation is 1:0.5–0.9:0.1–0.3:0.05–0.2. The solvent for reslurrying the cake from the second oxidation step is recycled from the isolating step for isolating the cake from the slurry obtained in the second extraction/post-oxidation step. The recycled solvent should be used in such an mount that at least 60% of the lower carboxylic acid contained in the slurry from the second oxidation step can be replaced with. The solvent for reslurrying the cake from the first extraction/post-oxidation step is recycled from the washing step for washing the cake resulted from the second extraction/post-oxidation step. The recycled solvent should be used in such an mount that at least 60% of the lower carboxylic acid contained in the slurry from the first extraction/post-oxidation step can be replaced with. The above-explained recycling of the solvent to extract the impurity improves the efficiency of the solvent usage and thus make it possible to minimize the loss of solvent.

Where Method 2 is employed for producing highly pure benzenedicarboxylic acid, the concentration of CBA as an impurity contained in the crude benzenedicarboxylic acids produced from the first oxidation, second oxidation, first extraction/post-oxidation and second extraction/post-oxidation is 0.1–0.4%, 0.05–0.15%, 0.01–0.03% and less than 0.005% respectively.

In Method 3, the ratio of [Co+Mn] to [Mr] is 1:0.01–0.2 and the total concentraion of heavy metal(s) added is 40–300 ppm. The concentration of heavy metal(s) employed in the first oxidation:first extraction/post-oxidation:second extraction/post-oxidation is 1:0.05–0.5:0.05–0.2. The solvent for reslurrying the cake from the first oxidation step is recycled from the isolating step for isolating the cake from the slurry obtained in the second extraction/post-oxidation step. The recycled solvent should be used in such an mount that at least 60% of the lower carboxylic acid contained in the slurry from the first oxidation step can be replaced with. The solvent for reslurrying the cake from the first extraction/post-oxidation step is recycled from the washing step for washing the cake resulted from the second extraction/post-oxidation step. The recycled solvent should be used in such an mount that at least 60% of the lower carboxylic acid contained in the slurry from the first extraction/post-oxidation step can be replaced with.

Where Method 3 is employed for producing highly pure benzenedicarboxylic acid, the concentration of CBA as impurity contained in the crude benzenedicarboxylic acids produced from the first oxidation, first extraction/post-oxidation and second extraction/post-oxidation is 0.04–0.15%, 0.01–0.05% and less than 0.0025% respectively.

It is possible to make choice of the above Method 1, 2 or 3 in consideration of a cost for installation and a loss of reactant and solvent. That is to say, for example, when it is desired to lower the cost for installation, Method 1 wherein the concentraion of the catalyst employed is relatively high may be preferably chosen and when it is desired to reduce the loss of xylene isomers and lower aliphatic carboxylic acid by oxidation, Method 2 wherein the oxidation step is carded out under the mild conditions may be preferably chosen.

Further, it is preferable to choose Method 3, where the moderate cost and loss of the reactant and solvent is required.

The main features and advantages of the present invention are as follows:

1) The extraction/post-oxidation step wherein the recycled solvent is employed to extract impurities under heating makes it possible to selectively oxidize the impurities while does not cause oxidation of solvent.

2) In the process for preparing benzenedicarboxylic acid comprising three or four oxidation steps in total, it is possible to selectively oxidize benzenedicarboxylic acid isomers at a moderate temperature with high yield by using an appropriate concentration of an improved catalyst system composed of cobalt, manganese and bromine together with one or more additional metals selected from nickel, chromium, zirconium and cerium in each oxidation step so that the rate limiting oxidation step in which toluic acid isomers and CBA are oxidized to benzenedicarboxylic acid can be accelerated while the side reaction which produces a high molecular weight colored organic compounds can be avoided.

3) The new method of introducing the reaction mixture into the reactor at high linear velocity of 6–30 m/s provides rapid and almost homogeneous distribution of the reaction mixture over the reaction zone. And the preliminary heating of the reaction mixture to a temperature between 150° C. and oxidation reaction temperature can eliminate the temperature gradient in the reaction zone and provides a steady reaction proceeding over the entire reaction volume in combination with the rapid mixing of the reaction mixture. This also makes it possible to reduce the loss of lower aliphatic carboxylic acid used as a solvent due to oxidation thereof.

These features and advantages of the present invention make it possible to produce highly purified benzenedicarboxylic acid isomer having color index of not more than 10+ H and containing less than 0.0025% of CBA isomer, a principal impurity, while minimizing the loss of solvent.

EXAMPLES

The present invention will be explained more in detail by way of the following non-limitative Examples. In Examples, all the metals are employed in the form of acetate and the bromine is in the form of hydrobromic acid, and the "%" is by weight unless otherwise indicated.

Examples 1 to 9 and Comparative Examples 1 to 7

(Method 1; oxidation step is carried out twice and then extraction/post-oxidation step is carried out once)

Example 1

A reaction mixture was prepared in a vessel made of titanium, which is equipped with an agitator and a heating jacket. The composition of the reaction mixture was 17% of p-xylene (1734 kg), 80.63% of acetic acid, 2% of water, 732 ppm of cobalt, 588 ppm of manganese, 70 ppm of nickel and 270 ppm of bromine. The reaction mixture was fed into the heater using a centrifugal pump and heated to 160° C. The preheated mixture was introduced at a linear rate of 20 m/s through 4 nozzles into the oxidation reactor ($V=10$ m$^3$) equipped with two parallel turbine agitators installed on a common shaft.

The oxidation was effected at 198° C. and 18 kg/cm² for 40 minutes.

The product from the first oxidation was fed into the second oxidation reactor and treated with the reflux from the crystallizer connected to the second oxidation reactor and a mixture of a vent gas from the first oxidation reactor and air. During the second oxidation, the water concentration was maintained at 10%. The purity of terephthalic acid obtained after the second oxidation was improved to 1.9 and 1.3 times in terms of content of 4-CBA and color index, respectively, compared with those of the product from the first oxidation.

The reaction mixture to be supplied to the first extraction/post-oxidation was prepared in a vessel equipped with a stirrer. The cake isolated from the product of the second oxidation, which has 15% of residual solvent, was introduced into the reactor and subjected to extraction of the impurities contained therein with a solvent. As the solvent for extraction, one which is recycled from the washing step for washing the cake obtained from the first extraction/post-oxidation step is used. The mount of the solvent recycled is such an mount that 85% of the total solvent contained in the product of the second oxidation is replaced with. The resulting slurry contained 25% of terephthalic acid.

The slurry was fed to the heater to heat up to about 230° C. and then sent to a vessel equipped with a stirrer and could maintain a constant temperature, where the slurry was maintained for 10 minutes (The first extraction). And the heat-treated slurry was fed to the first extraction/post-oxidation reactor where the slurry was treated with a mixture of the vent-gas from the first oxidation reactor and air at 200° C., and at the same time a hydrobromic acid/acetic acid solution composed of cobalt, manganese, nickel, 95% of acetic acid, 4.875% of water and 0.125% of hydrobromic acid was fed to the reactor (The first post-oxidation). Finally, the composition of the reaction mixture in the first extraction/post-oxidation was 20% of terephthalic acid, 7% of water, 132 ppm of [Co+Mn+Ni] and 212 ppm of bromine.

The reaction time of the first post-oxidation was 20 minutes. After completion of the reaction., the product was crystallized at 105° C. under the atmospheric pressure in a collector. The solids were isolated by centrifugation, washed with fresh acetic acid and dried. The final product from the post-oxidation step contained 25 ppm of 4-CBA and had a color index of 8° H. The yield was 98%. The total oxidation time from the first oxidation to the first extracton/post-oxidation was 80 minutes.

According to the process of the invention, the very rapid introduction of the reaction mixture into the reactor makes it possible to attain a rapid homogeneous distribution of the temperature and concentration of the reactants in the reactor and the use of the specific catalysts as well as the adoption of the extraction step using the recycled solvent make it possible to selectively oxidize specific compounds to produce highly pure phthalic acid isomers containing not more than 25 ppm of CBA isomer and having less than 10° H of color index and to proceed with the process rapidly. The each step can be completed within about 10 to 40 minutes.

The oxidation conditions and results in Example 1 are shown in Table 1.

Example 2

The procedure of Example 1 was repeated except that 40 ppm of Ni, 20 ppm of Cr, 30 ppm of Zr and 40 ppm of Ce were employed instead of 70 ppm of Ni and the reaction times and temperatures were changed as shown in Table 1. The finally produced terephthalic acid contained 15 ppm of 4-CBA and had the color index of 4° H. The oxidation conditions and results in Example 2 are shown in Table 1.

Example 3

The procedure of Example 1 was repeated except that 120 ppm of Zr was employed instead of 70 ppm of Ni and the reaction times and temperatures were changed as shown in Table 1. The finally produced terephthalic acid contained 24 ppm of 4-CBA and had the color index of 8° H. The oxidation conditions and results in Example 3 are shown in Table 1.

Example 4

The procedure of Example 1 was repeated except that 120 ppm of Ce was employed instead of 70 ppm of Ni and the reaction times and temperatures were changed as shown in Table 1. The finally produced terephthalic acid contained 22 ppm of 4-CBA and had the color index of 7° H. The oxidation conditions and results in Example 4 are shown in Table 1.

Example 5

The procedure of Example 1 was repeated except that the amount of the nickel was increased to 100 ppm from 70 ppm and the reaction times and temperatures were changed as shown in Table 1. The finally produced terephthalic acid contained 20 ppm of 4-CBA and had the color index of 7° H. The oxidation conditions and results in Example 5 are shown in Table 1.

Comparative Example 1

The procedure of Example 1 was repeated except that no Ni was added and the reaction times and temperatures were changed as shown in Table 1. The finally produced terephthalic acid contained 25 ppm of 4-CBA and had high color index of 46° H. The oxidation conditions and results in Comparative Example 1 are shown in Table 1.

Comparative Example 2

The procedure of Comparative Example 1 was repeated except that the introduction rate of the reaction mixture was reduced from 28 m/s to 1 m/s and the extraction time was changed from 10 minutes to 1 minute. The finally produced terephthalic acid contained 650 ppm of 4-CBA and had the color index of 26° H. The oxidation conditions and results in Comparative Example 2 are shown in Table 1.

Comparative Example 3

The procedure of Example 5 was repeated except that 50 ppm of Ni and 50 ppm of Cr were employed instead of 100 ppm of Ni and the catalyst concentration, [Co+Mn+Ni+Cr] in the first post-oxidation reaction and bromine concentration were changed from 132 ppm and 212 ppm to 21 ppm and 32 ppm, respectively. The finally produced terephthalic acid contained 15 ppm of 4-CBA and had the color index of 4° H. The oxidation conditions and results in Comparative Example 3 are shown in Table 1.

Comparative Example 4

The procedure of Example 1 was repeated except that no Ni was added and the temperature of introducing the reaction mixture and the heating and reaction temperatures in the first extraction/post-oxidation were changed from 160° C., 230° C. and 200° C. to 60° C., 180° C. and 180° C., respectively. The finally produced terephthalic acid contained 222 ppm of 4-CBA and had the color index of 21° H. The oxidation conditions and results in Comparative Example 4 are shown in Table 1.

Example 6

The procedure of Example 1 was repeated except that m-xylene was employed instead of p-xylene. The finally produced isophthalic acid contained 15 ppm of 3-CBA and had the color index of 10° H. The oxidation conditions and results in Example 6 are shown in Table 1.

Comparative Example 5

The procedure of Example 6 was repeated except that no Ni was added, the linear velocity of introducing the reaction mixture was reduced from 20 m/s to 1 m/s and the holding time in the first extraction step was reduced from 10 minutes to 3 minutes. The finally produced isophthalic acid contained 160 ppm of 3-CBA and had the color index of 48° H. The oxidation conditions and results in Comparative Example 5 are shown in Table 1.

Example 7

The procedure of Example 1 was repeated except that o-xylene was employed instead of p-xylene and 40 ppm of Ni, 20 ppm of Cr, 30 ppm of Zr and 40 ppm of Ce were employed instead of 70 ppm of Ni. The finally produced phthalic acid contained 20 ppm of 2-CBA and had the color index of 10° H. The oxidation conditions and results in Example 7 are shown in Table 1.

Comparative Example 6

The procedure of Example 1 was repeated except that p-xylene was replaced with o-xylene and the rate of introducing the reaction mixture was reduced from 20 m/s to 1 m/s. The finally produced phthalic acid contained 28 ppm of 2-CBA and had the color index of 20° H. The oxidation conditions and results in Comparative Example 6 are shown in Table 1.

Examples 8 to 17 and Comparative Examples 7 to 8

(Method 2; oxidation step is carried out twice and then extraction/post-oxidation step is carried out twice)

Example 8

In this Example, a continuous unit consisting of a reaction mixture collector, a metering pump, reactor equipped with an agitator, a condenser and a crystallizer was employed to oxidize p-xylene. A reaction mixture of which composition was 14% of p-xylene (330 g), 83.9% of acetic acid, 2% of water, 254 ppm of cobalt, 127 ppm of manganese, 23 ppm of zirconium and 632 ppm of bromine was introduced into the reaction mixture collector.

The reaction mixture was preliminarily heated to 160° C. and then fed into the reactor (1 l) whilst supplying air thereto. The mixture was reacted at 192° C. while monitoring the contents of the gas, i.e., $O_2$, CO or $CO_2$, temperature, pressure, and the consumption rates of reaction mixture and air and sampling the reaction product at an appropriate interval. The samples were separated to liquid and solid phases and analyzed quantatively and qualitively using common techniques such as chromatography, polarography and photometric methods.

After completion of the first oxidation, the slurry resulted from the first oxidation was fed into the second oxidation reactor and treated at 185° C. with the air and the vent-gas from the first oxidation reactor and the reflux from the crystallizer connected to the second oxidation reactor. The second oxidation product was isolated to give a cake which was reslurried with the mother liquor recycled from the isolation step for isolating the cake from the slurry obtained from the second extraction/post-oxidation and then fed into the first extraction/post-oxidation reactor. The contents in the first extraction/post-oxidation reactor was heated to 230° C., maintained for 7 minutes and cooled to 198° C., and then was subjected to oxidation reaction. The concentration of the catalyst used in the oxidation was 5 times lower than that of the catalyst used in the first oxidation. After the first extraction/post-oxidation step, the concentration of CBA contained in the product terephthalic acid reduced from 950 ppm (after the second oxidation) to 210 ppm and the color index reduced from 9° H to 7° H.

The cake isolated from the first extraction/post-oxidation product was reslurried with the acetic acid recycled from the washing step for washing the cake isolated from the second extraction/post-oxidation and then fed into the second extraction/post-oxidation reactor. The contents in the second extraction/post-oxidation reactor was heated to 230° C., maintained for 7 minutes and cooled to 198° C., and then was subjected to oxidation reaction. The concentration of the catalyst used in the second post-oxidation was 10 times lower than that of the catalyst used in the first oxidation. The second post-oxidation product was cooled and terephthalic acid was isolated therefrom and washed with fresh acetic acid. The oxidation conditions and results in Example 9 are shown in Table 2.

In this Example, highly purified terephthalic acid containing 14 ppm of 4-CBA and having a color index of 6° H can be produced.

Example 9

The procedure of Example 8 was repeated except that zirconyl chloride was employed instead of zirconyl bromide. The change of the zirconium compound from zirconyl bromide to zirconyl chloride produced no change in the color index of the produced terephthalic acid, but the content of 4-CBA was reduced from 14 ppm to 11 ppm. The oxidation conditions and results in Example 9 are shown in Table 2.

Example 10

The procedure of Example 8 was repeated except that nickel chloride hexahydrate was employed instead of zirconium bromide. When comparing with the result of Example 8, the content of 4-CBA was similar thereto and the color index of the produced terephthalic acid was lower. The oxidation conditions and results in Example 10 are shown in Table 2.

Example 11

The procedure of Example 8 was repeated except that cerium compound was employed instead of zirconium compound. Highly purified terephthalic acid was obtained. The oxidation conditions and results in Example 11 are shown in Table 2.

Example 12

The procedure of Example 8 was repeated except that chromium compound was employed instead of zirconium compound. Highly purified terephthalic acid was obtained. The oxidation conditions and results in Example 12 are shown in Table 2.

Example 13

The procedure of Example 8 was repeated except that a mixture of zirconium, nickel and chromium compounds was employed instead of zirconium compound. When comparing with the result of Example 8, the content of 4-CBA and the color index of the produced terephthalic acid was lowered. The oxidation conditions and results in Example 13 are shown in Table 2.

Comparative Example 7

The procedure of Example 13 was repeated except that no heavy metal was added. The quality of the produced terephthalic acid did not comply with the requirement of high purity. The oxidation conditions and results in Comparative Example 7 are shown in Table 2.

Examples 14 and 15

The procedure of Example 8 was repeated except that the capacity of the reactor was changed from 1 l to 10 m³. The reactor is equipped with two parallel agitators and a nozzle for controlling the rate and direction of introduction of the mixture. The first and second oxidations were carried out at the same temperature in Example 8 and the first and second post-oxidations were carried out at 188°–199° C. The concentration of the catalyst was increased to about 2 times in Example 14 and about 1.5 times in Example 15 compared with Example 8. As results, highly purified terephthalic acids containing 10 ppm and 24 ppm, respectively were obtained. The oxidation conditions and results in Examples 14 and 15 are shown in Table 2. Comparative Example 8

The procedure of Example 14 was repeated except that the reaction mixture was fed at a rate of 5 m/s through 4 branch pipes instead of using a nozzle and reaction temperatures and times were changed as shown in Table 2. The color index of the produced terephthalic acid contained was as high as 28° H. The oxidation conditions and results in Comparative Example 8 are shown in Table 2.

Examples 16 and 17

The procedure of Example 8 was repeated except that m-xylene and o-xylene were oxidized in stead of p-xylene, respectively, and nickel was employed instead of zirconium. As results, highly purified terephthalic and isophthalic acids containing 12 ppm and 23 ppm of CBA and having color index of 6° H and 10° H, respectively were obtained. The oxidation conditions and results in Examples 16 and 17 are shown in Table 2.

Examples 18 to 20

(Method 3: oxidation step is carded out once and then extraction/post-oxidation step is carded out twice)

Example 18

In this Example, p-xylene was oxidized in accordance with Method 3. A reaction mixture of which composition was 14% of p-xylene (378 g), 83.8% of acetic acid, 2% of water, 618 ppm of cobalt, 292 ppm of manganese, 61 ppm of nickel and 1416 ppm of bromine was introduced into the reaction mixture collector.

The reaction mixture was preliminarily heated to 160° C. and then continuously fed into the reactor whilst supplying air thereto. The mixture was reacted at 188° C. while monitoring the contents of the gas, i.e., $O_2$, CO or $CO_2$, temperature, pressure, and the consumption rates of reaction mixture and air and sampling the reaction product at an appropriate interval. The samples were separated into liquid and solid phases and analyzed quantatively and qualitively using common techniques such as chromatography, polarography and photometric methods.

After completion of the first oxidation, the slurry resulted from the first oxidation was cooled to 100° C. to give cake, which was reslurried with the mother liquor recycled from the isolation step for isolating the cake from the slurry obtained from the second extraction/post-oxidation and then fed into the first extraction/post-oxidation reactor. The contents in the first extraction/post-oxidation reactor was heated to 240° C., maintained for 15 minutes and cooled to 198° C. followed by subjecting to oxidation reaction. The concentrations of the heavy metals and bromine in the catalyst used in the oxidation were 7 times and 9 times lower than those of the catalyst used in the first oxidation.

The cake isolated from the first extraction/post-oxidation product was reslurried with the acetic acid recycled from the washing step for washing the cake isolated from the second extraction/post-oxidation and then fed into the second extraction/post-oxidation reactor. The contents in the second extraction/post-oxidation reactor was heated to 240° C., maintained for 15 minutes and cooled to 198° C. followed by subjecting to oxidation. The concentration of the catalyst used in the second post-oxidation was 10 times lower than that of the catalyst used in the first oxidation. The second post-oxidation product was cooled and terephthalic acid was isolated therefrom and washed with fresh acetic acid. The oxidation conditions and results in Example 18 are shown in Table 3.

Example 19

The procedure of Example 18 was repeated except that the catalysts recovered from the mother liquor of the first oxidation was used instead of fresh catalysts. As a result, there could be obtained a highly purified terephthalic acid. The oxidation conditions and results in Example 19 are shown in Table 3.

Example 20

The procedure of Example 18 was repeated except that 31 ppm of nickel and 31 ppm of zirconium were employed instead of 61 ppm of nickel. And the concentration of the catalyst used in the first and second post-oxidations were reduced to 8 times and 12 times, respectively, compared with those of in the first oxidation. As a result, there could be obtained a highly purified terephthalic acid. The oxidation conditions and results in Example 20 are shown in Table 3.

TABLE 1

| Example No. | Catalyst conc. (ppm) Co | Mn | Mt | Br | First oxidation Oxidation conditions Temp. T(°C.) | Time t(min) | W* m/s | Second Oxidation Oxidation conditions Temp. T(°C.) | Time t(min) | First extraction/post-oxidation Extraction conditions Temp. T(°C.) | Time t(min) | Oxidation conditions Temp. T(°C.) | Time t(min) | Results Quality CBA (ppm) | Color (°H) |
|---|---|---|---|---|---|---|---|---|---|---|---|---|---|---|---|
| Ex. 1 | 732 | 588 | Ni70 | 2270 | 198 | 40 | 20 | 180 | 20 | 230 | 10 | 200 | 20 | 25 | 8 |
| Ex. 2 | 700 | 580 | Ni40 Cr20 Zr30 Ce40 | 2270 | 198 | 35 | 20 | 190 | 20 | 230 | 10 | 200 | 20 | 15 | 4 |
| Ex. 3 | 700 | 580 | Zr120 | 2270 | 198 | 35 | 20 | 185 | 20 | 230 | 10 | 200 | 20 | 24 | 8 |
| Ex. 4 | 700 | 580 | Ce120 | 2270 | 198 | 35 | 20 | 185 | 20 | 230 | 10 | 200 | 20 | 22 | 7 |
| Ex. 5 | 950 | 550 | Ni100 | 2500 | 200 | 35 | 16 | 195 | 18 | 210 | 25 | 188 | 22 | 20 | 7 |
| C. Ex. 1 | 700 | 580 | — | 2270 | 198 | 35 | 28 | 180 | 20 | 230 | 10 | 200 | 20 | 25 | 46 |

TABLE 1-continued

| Example No. | First oxidation Catalyst conc. (ppm) | | | | First oxidation Oxidation conditions | | | Second Oxidation Oxidation conditions | | First extraction/post-oxidation Extraction conditions | | First extraction/post-oxidation Oxidation conditions | | Results Quality | |
|---|---|---|---|---|---|---|---|---|---|---|---|---|---|---|---|
| | Co | Mn | Mt | Br | Temp. T(°C.) | Time t(min) | W* m/s | Temp. T(°C.) | Time t(min) | Temp. T(°C.) | Time t(min) | Temp. T(°C.) | Time t(min) | CBA (ppm) | Color (°H) |
| C. Ex. 2 | 700 | 580 | — | 2270 | 198 | 35 | 1.0 | 180 | 20 | 230 | 1.0 | 200 | 20 | 650 | 26 |
| C. Ex. 3 | 950 | 550 | Ni50 Cr50 | 2500 | 186 | 35 | 9 | 180 | 60 | 230 | 10 | 200 | 60 | 421 | 9 |
| C. Ex. 4 | 732 | 588 | — | 2270 | 218 | 35 | 20 | 180 | 20 | 180 | 10 | 180 | 60 | 222 | 21 |
| Ex. 6 | 732 | 588 | Ni70 | 2270 | 198 | 40 | 20 | 180 | 20 | 230 | 10 | 200 | 20 | 15 | 10 |
| C. Ex. 5 | 710 | 580 | — | 2270 | 198 | 35 | 1.0 | 180 | 20 | 230 | 3.0 | 200 | 20 | 160 | 48 |
| Ex. 7 | 700 | 580 | Ni40 Cr20 Zr30 Ce40 | 2270 | 198 | 35 | 20 | 190 | 20 | 230 | 20 | 200 | 20 | 20 | 20 |
| C. Ex. 6 | 732 | 588 | Ni70 | 2270 | 198 | 40 | 1.0 | 180 | 20 | 230 | 10 | 200 | 20 | 28 | 20 |

W*: Linear velocity of introducing reaction mixture

TABLE 2

| Example No. | First oxidation Catalyst conc. (ppm) | | | | First oxidation Oxidation condition | | | Second oxidation Oxidation conditions | | First extraction/post-oxidation Extraction conditions | | First extraction/post-oxidation Oxidation conditions | |
|---|---|---|---|---|---|---|---|---|---|---|---|---|---|
| | Co | Mn | Mt | Br/Cl | temp. T °C. | time t(min) | W* m/s | temp. T °C. | time t(min) | temp. T °C. | time t(min) | temp. T °C. | time t(min) |
| Ex. 8 | 254 | 127 | Zr 23 | 632/— | 192 | 38 | 12 | 185 | 20 | 230 | 7 | 198 | 20 |
| Ex. 9 | 254 | 127 | Zr 23 | 612/28 | 192 | 38 | 12 | 185 | 20 | 230 | 7 | 198 | 20 |
| Ex. 10 | 254 | 127 | Ni 24 | 612/35 | 200 | 38 | 12 | 185 | 20 | 240 | 7 | 200 | 20 |
| Ex. 11 | 254 | 127 | Ce 24 | 632/— | 192 | 38 | 12 | 185 | 20 | 230 | 7 | 198 | 20 |
| Ex. 12 | 254 | 127 | Cr 24 | 632/— | 192 | 38 | 12 | 185 | 20 | 230 | 7 | 198 | 20 |
| Ex. 13 | 254 | 127 | Zr 12 Ni 6 Cr 6 | 632/— | 192 | 38 | 12 | 185 | 20 | 230 | 7 | 198 | 20 |
| C. Ex. 7 | 254 | 127 | — | 632/— | 192 | 38 | 12 | 185 | 20 | 230 | 7 | 198 | 20 |
| Ex. 14 | 500 | 250 | Ni 45 | 920/— | 192 | 40 | 18 | 185 | 18 | 225 | 10 | 198 | 15 |
| Ex. 15 | 400 | 200 | Ni 38 | 640/— | 192 | 40 | 16 | 185 | 20 | 230 | 5 | 188 | 20 |
| C. Ex. 8 | 500 | 250 | Ni 45 | 920/— | 192 | 40 | 5 | 185 | 18 | 225 | 10 | 198 | 15 |
| Ex. 16 | 254 | 127 | Ni 24 | 612/— | 200 | 40 | 12 | 185 | 20 | 240 | 7 | 200 | 20 |
| Ex. 17 | 254 | 127 | Ni 24 | 810/8 | 200 | 48 | 12 | 185 | 25 | 225 | 6 | 200 | 26 |

| Example No. | Second extraction/post-oxidation Extraction conditions | | Second extraction/post-oxidation Oxidation conditions | | Results Quality | |
|---|---|---|---|---|---|---|
| | temp. T °C. | time t(min) | temp. T °C. | time t(min) | CBA (ppm) | Color (°H) |
| Ex. 8 | 230 | 7 | 198 | 20 | 14 | 6 |
| Ex. 9 | 230 | 7 | 198 | 20 | 11 | 5 |
| Ex. 10 | 240 | 7 | 200 | 20 | 18 | 3.5 |
| Ex. 11 | 230 | 7 | 198 | 20 | 23 | 6 |
| Ex. 12 | 230 | 7 | 198 | 20 | 25 | 5 |
| Ex. 13 | 230 | 7 | 198 | 20 | 10 | 3.5 |
| C. Ex. 7 | 230 | 7 | 198 | 20 | 60 | 7 |
| Ex. 14 | 225 | 5 | 188 | 15 | 10 | 4 |
| Ex. 15 | 230 | 12 | 199 | 18 | 24 | 5 |
| C. Ex. 8 | 225 | 5 | 188 | 15 | 32 | 28 |
| Ex. 16 | 225 | 5 | 188 | 15 | 12 | 6 |
| Ex. 17 | 225 | 5 | 190 | 22 | 23 | 10 |

W*: Linear velocity of introducing reaction mixture

TABLE 3

| Example No. | First oxidation Catalyst conc. (ppm) | | | | First oxidation Oxidation conditions | | | First extraction/post-oxidation Extraction conditions | | First extraction/post-oxidation Oxidation conditions | |
|---|---|---|---|---|---|---|---|---|---|---|---|
| | Co | Mn | Mt | Br | Temp. T(°C.) | Time t(min) | W* m/s | Temp. T(°C.) | Time t(min) | Temp. T(°C.) | Time t(min) |
| Ex. 18 | 618 | 292 | Ni61 | 1416 | 188 | 52 | 12 | 240 | 15 | 180 | 25 |
| Ex. 19 | 618 | 292 | Ni61 | 1416 | 192 | 52 | 12 | 230 | 15 | 185 | 25 |
| Ex. 20 | 618 | 292 | Ni31 Zr31 | 1114 116 | 192 | 46 | 12 | 240 | 15 | 185 | 25 |

Second

TABLE 3-continued

| | extraction/post-oxidation | | | | Results Quality | |
|---|---|---|---|---|---|---|
| | Extraction conditions | | Oxidation conditions | | | |
| Example No. | Temp. T(°C.) | Time t(min) | Temp. T(°C.) | Time t(min) | CBA (ppm) | Color (°H) |
| Ex. 18 | 240 | 15 | 198 | 25 | 6 | 8 |
| Ex. 19 | 235 | 15 | 198 | 20 | 6 | 8 |
| Ex. 20 | 240 | 8 | 198 | 20 | 5 | 7 |

W*: Linear velocity of introducing reaction mixture

What is claimed is:

1. A process for producing highly purified benzenedicarboxylic acid isomers without an additional catalytic reductive purification step, which comprises (a) an oxidation step wherein xylene isomer is oxidized with molecular oxygen or molecular oxygen containing gas in the presence of a catalyst system composed of cobalt, manganese, bromine and at least one selected from nickel, chromium, zirconium and cerium in lower aliphatic carboxylic acid; and (b) an extraction/post-oxidation step wherein the oxidation product is crystallized to give cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-80° C. lower than that of said heating, each of said oxidation and extraction/post-oxidation being carried out once or twice, provided that any one or both of said steps should be carried out twice.

2. The process according to claim 1 characterized in that which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in lower aliphatic carboxylic acid; (b) the second oxidation step wherein the product obtained from the first oxidation step is reoxidized with said catalyst system; and (c) the first extraction/post-oxidation step wherein the product obtained from the second oxidation step is crystallized to give a cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-80° C. lower than that of said heating.

3. The process according to claim 1 characterized in that which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in lower aliphatic carboxylic acid; (b) the second oxidation step wherein the product obtained from the first oxidation step is reoxidized with said catalyst system; (c) the first extraction/post-oxidation step wherein the product obtained from the second oxidation step is crystallized to give cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-80° C. lower than that of said heating; and (d) the second extraction/post-oxidation step wherein the product obtained from the first extraction/post-oxidation step is crystallized to give a cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-80° C. lower than that of said heating.

4. The process according to claim 1 characterized in that which comprises (a) the first oxidation step wherein xylene isomer is oxidized with molecular oxygen or molecular oxygen containing gas in the presence of a catalyst system composed of cobalt, manganese, bromine and at least one selected from nickel, chromium, zirconium and cerium in lower aliphatic carboxylic acid; (b) the first extraction/post-oxidation step wherein the product obtained from the first oxidation step is crystallized to give cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-80° C. lower than that of said heating; and (c) the second extraction/post-oxidation step wherein the product obtained from the first extraction/post-oxidation step is crystallized to give cake of crude benzenedicarboxylic acid isomer, the cake is reslurried by adding lower aliphatic carboxylic acid solvent thereto followed by heating in order to extract impurities contained therein into the solvent, and the resulting slurry is oxidized with said catalyst system at a temperature of 2°-° C. lower than that of said heating.

5. The process according to any one of claims 1 to 4, wherein the reaction mixture to be introduced into the first oxidation reactor is preliminarily heated to a temperature between 150° C. and that of the first oxidation step.

6. The process according to claim 2, wherein the lower aliphatic carboxylic acid solvent to reslurry the cake isolated from the second oxidation product is recycled from the washing step for washing the cake isolated from the first extraction/post-oxidation product.

7. The process according to claim 3, wherein the lower aliphatic carboxylic acid solvent employed to reslurry the cake isolated from the second oxidation product is recycled from the isolation step for isolating the cake from the slurry obained from the second extraction/post-oxidation step and the lower aliphatic carboxylic acid solvent employed to reslurry the cake isolated from the first extraction/post-oxidation product is recycled from the washing step for washing the cake isolated from the second extraction/post-oxidation product.

8. The process according to claim 4, wherein the lower aliphatic carboxylic acid solvent employed to reslurry the cake isolated from the first oxidation product is recycled from the isolation step for isolating the cake from the slurry obained from the second extraction/post-oxidation step and the lower aliphatic carboxylic acid solvent employed to reslurry the cake isolated from the first extraction/post-oxidation product is recycled from the washing step for washing the cake isolated from the second extraction/post-oxidation product.

9. The process according to claim 2 or 3, wherein the first and second oxidation are carried out at 150°–230° C. for 20–60 minutes.

10. The process according to claim 4, wherein the first oxidation is carried out at 150°–230° C. for 20–60 minutes.

11. The process according to any one of claims 2 to 4, wherein the reaction mixture is fed into the first oxidation reactor at a linear velocity of 6–30 m/s in a counter direction to the revolution direction of the contents in the reactor.

12. The process according to claim 2, wherein the ratio of the concentration of the heavy metals selected from nickel, chromium, zirconium and cerium to the total concentration of cobalt and manganese is 0.01–0.2:1 and the total concentration of said heavy metals is 50–300 ppm.

13. The process according to claim 2, wherein the ratio of the concentration of the heavy metals selected from nickel, chromium, zirconium and cerium employed in the first oxidation, second oxidation and first post-oxidation is 1:0.5–0.9:0.05–0.2.

14. The process according to claim 3, wherein the ratio of the concentration of the heavy metals selected from nickel, chromium, zirconium and cerium to the total concentration of cobalt and manganese is 0.01–0.2:1 and the total concentration of said heavy metals is 30–200 ppm.

15. The process according to claim 3, wherein the ratio of the concentration of the heavy metals selected from nickel, chromium, zirconium and cerium employed in the first oxidation, second oxidation, first post-oxidation and second oxidation is 1:0.5–0.9:0-.1–0.3:0.05–0.2.

16. The process according to claim 4, wherein the ratio of the concentration of the heavy metals selected from nickel, chromium, zirconium and cerium to the total concentration of cobalt and manganese is 0.01–0.2:1 and the total concentration of said heavy metals is 40–300 ppm.

17. The process according to claim 4, wherein the ratio of the concentration of the heavy metals selected from nickel, chromium, zirconium and cerium employed in the first oxidation, second oxidation and first post-oxidation is 1:0.05–0.5:0.05–0.2.

18. The process according to claim 1, wherein the bromine compound is a bromine compound alone or a mixture of bromine compound and chlorine compound in a ratio of 1:0.001–0.5 in terms of bromine and chlorine.

19. The process according to any one of claims 6 to 8, wherein the mount of the recycled lower carboxylic acid is such an mount that at least 60% of the lower carboxylic acid contained in the slurry from the previous oxidation step can be replaced with.

* * * * *

UNITED STATES PATENT AND TRADEMARK OFFICE
CERTIFICATE OF CORRECTION

PATENT NO. : 5,359,133
DATED : October 25, 1994
INVENTOR(S) : NAZIMOK et al

It is certified that error appears in the above-identified patent and that said letters patent is hereby corrected as shown below:

Column 2, line 26, delete "crashing" insert --crushing--;
Column 2, line 35, delete "mount" insert --amount--;
Column 2, lines 66 and 68, delete "carded" insert --carried--.
Column 4, lines 14, 22, 41, 43, 47, 48, 49, 50 and 51, delete "carded" insert --carried--;
Column 4, line 44, delete "my" insert --may--.
Column 5, lines 16 and 60 delete "carded" insert --carried--;
Column 5, line 65, delete "alter" insert --after--.
Column 6, lines 1 and 6, delete "carded" insert --carried--;
Column 6, line 17, delete "Wittic" insert --toluic--.
Column 6, lines 22 and 59, delete "mount" insert --amount--.
Column 7, lines 11, 18, 41, 48, delete "mount" insert --amount--;
Column 7, line 32, delete "[Mr]" insert --[Mt]--;
Column 7, line 67, delete "carded" insert --carried--.
Column 8, line 42, delete "10+H" and insert --10°H--.
Column 9, lines 22 and 23, delete "mount" insert --amount--.
Column 13, lines 20 and 21 delete "Comparative Example 8" and insert on a separate line --Comparative Example 8--;
Column 13, lines 41 and 42 delete "carded" insert --carried--.

Column 18, line 46, delete "2°-°C." insert --2°-80°C.--.

Column 20, lines 30 and 31, delete "mount" insert --amount--.

Signed and Sealed this

Seventh Day of March, 1995

Attest:

BRUCE LEHMAN

Attesting Officer    *Commissioner of Patents and Trademarks*